US012103970B2

(12) United States Patent
Wu et al.

(10) Patent No.: US 12,103,970 B2
(45) Date of Patent: Oct. 1, 2024

(54) CAR-T CELLS WITH HUMANIZED CD19 ScFv

(71) Applicants: ProMab Biotechnologies, Inc., Richmond, CA (US); Forevertek Biotechnology Co., Ltd, Changsha (CN)

(72) Inventors: Lijun Wu, Berkeley, CA (US); Vita Golubovskaya, Pinole, CA (US)

(73) Assignees: ProMab Biotechnologies, Inc., Richmond, CA (US); Forevertek Biotechnology Co., Ltd, Changsha (CN)

( * ) Notice: Subject to any disclaimer, the term of this patent is extended or adjusted under 35 U.S.C. 154(b) by 507 days.

(21) Appl. No.: 17/465,093

(22) Filed: Sep. 2, 2021

(65) Prior Publication Data

US 2021/0395364 A1    Dec. 23, 2021

Related U.S. Application Data

(63) Continuation of application No. PCT/US2020/019819, filed on Feb. 26, 2020.
(Continued)

(51) Int. Cl.
*C07K 16/28*     (2006.01)
*A61K 35/17*     (2015.01)
(Continued)

(52) U.S. Cl.
CPC .......... *C07K 16/2803* (2013.01); *A61K 35/17* (2013.01); *C07K 14/7051* (2013.01);
(Continued)

(58) Field of Classification Search
CPC ............ C07K 16/2803; C07K 14/7051; C07K 14/70521; C07K 14/70578;
(Continued)

(56) References Cited

U.S. PATENT DOCUMENTS

2018/0312588 A1    11/2018    Wiltzius et al.

FOREIGN PATENT DOCUMENTS

| CN | 110396129 A | 11/2019 |
| EP | 3539986 B1 | 4/2022 |

OTHER PUBLICATIONS

International Search Report for PCT Application No. PCT/US2020/019819. Mail Date: Jun. 10, 2020. 3 pages.

*Primary Examiner* — Jeremy C Flinders
*Assistant Examiner* — Thomas R. Amick
(74) *Attorney, Agent, or Firm* — Perkins Coie LLP; Viola Kung

(57) ABSTRACT

The present invention is directed to a humanized CD19 single-chain variable fragment (scFv), comprising the amino acid sequence of SEQ ID NO: 8. The present invention is also directed to a CD19 chimeric antigen receptor fusion protein comprising from N-terminus to C-terminus: (i) a single-chain variable fragment (scFv) of the present invention, (ii) a transmembrane domain, (iii) at least one co-stimulatory domains, and (iv) an activating domain. The humanized anti-CD19 scFv of the present invention exhibits selective and high-affinity binding to CD19. CD19-CAR T cells based on humanized scFv of the present invention are useful to treat patients with B-cell malignancies including leukemia and lymphomas.

14 Claims, 5 Drawing Sheets

Specification includes a Sequence Listing.

Related U.S. Application Data

(60) Provisional application No. 62/814,234, filed on Mar. 5, 2019.

(51) Int. Cl.
  *C07K 14/705* (2006.01)
  *C07K 14/725* (2006.01)
  *A61K 38/00* (2006.01)

(52) U.S. Cl.
  CPC .............. *C07K 14/70521* (2013.01); *C07K 14/70578* (2013.01); *A61K 38/00* (2013.01); *C07K 2317/56* (2013.01); *C07K 2317/622* (2013.01); *C07K 2319/03* (2013.01)

(58) Field of Classification Search
  CPC .......... C07K 2317/56; C07K 2317/622; C07K 2319/03; C07K 2317/24; C07K 2319/33; A61K 35/17; A61K 38/00; A61K 39/4611; A61K 39/4631; A61K 2239/31; A61K 2239/38; A61K 39/464412; A61K 2039/585; A61K 2239/48; A61P 35/02
  See application file for complete search history.

CAR-T CELLS WITH HUMANIZED CD19 ScFv

This application is a continuation of PCT/US2020/019819, filed Feb. 26, 2020; which claims the priority of U.S. Provisional Application No. 62/814,234, filed Mar. 5, 2019. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Feb. 25, 2020, and a size of 18.6 kilobytes. The Sequence Listing filed via EFS-Web is part of the specification and is hereby incorporated in its entirety by reference herein.

FIELD OF THE INVENTION

The present invention relates to humanized CD19 ScFv (clone 6, PMC288) derived from mouse FMC63 antibody. The present invention also relates to CD19-CAR-T cells using the humanized CD19 ScFv of the present invention. The CD19-CAR-T cells are useful in the cell therapy for treating leukemia and lymphoma patients.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CAR (Chimeric antigen receptor) constructs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug") [1, 3, 4].

CARs typically consist of a monoclonal antibody-derived single-chain variable fragment (scFv) at the N-terminal part, hinge, transmembrane domain and a number of intracellular co-activation domains: (i) CD28, (ii) CD137 (4-1BB), CD27, or other co-stimulatory domains, in tandem with an activation CD3-zeta domain. (FIG. 1) [1,2]. The evolution of CARs went from first generation (with no co-stimulation domains) to second generation (with one co-stimulation domain) to third generation CAR (with several co-stimulation domains). Generating CARs with two costimulatory domains (the so-called $3^{rd}$ generation CAR) have led to increased cytolytic CAR-T cell activity, improved persistence of CAR-T cells leading to its augmented antitumor activity.

FIG. 1 illustrates the structures of CAR. The left panel shows the structure of the first generation of CAR (no costimulatory domains). The middle panel shows the structure of the second generation of CAR (one co-stimulation domain CD28 or 4-BB). The right panel shows the third generation of CAR (two or several co-stimulation domains) [6].

Natural killer cells, or NK cells, are a type of cytotoxic lymphocyte critical to the innate immune system. The role NK cells play is analogous to that of cytotoxic T cells in the vertebrate adaptive immune response. NK cells provide rapid responses to virus-infected cells, acting at around 3 days after infection, and respond to tumor formation.

CD19

CD19 is a B-cell type lymphocyte antigen which is expressed on all B-cell malignancies, including acute lymphoblastic leukemia (ALL), chronic lymphoblastic leukemia (CLL), and Non-Hodgkin lymphomas. This universal expression among leukemia and lymphomas made this antigen an attractive target for targeting with CAR-T cells [3].

CD19 Structure and Signaling

The human CD19 protein is a 95 kDa transmembrane glycoprotein which consists of 556 amino-acids: 20-291-extracellular domain; 292-313-transmembrane domain; 314-556-cytoplasmic domain as shown below (extracellular domain underlined). It belongs to immunoglobulin superfamily proteins and mediates B cell receptor, BCR-dependent and independent signaling. CD19 binds to BCR and other cell surface protein to modulate intracellular signaling through binding other kinases and binding partners. CD19 signaling relates to Src-family kinase, PI3Kinase, Abl, AKT-dependent signaling. CD19 is a biomarker of B-cells mediating survival signaling and immune responses.

```
                                           (SEQ ID NO: 1)
          10          20          30          40
MPPPRLLFFL  LFLTPMEVRP  EEPLVVKVEE  GDNAVLQCLK 50          60          70          80
GTSDGPTQQL  TWSRESPLKP  FLKLSLGLPG  LGIHMRPLAI 90         100         110         120
WLFIFNVSQQ  MGGFYLCQPG  PPSEKAWQPG  WTVNVEGSGE 130         140         150         160
LFRWNVSDLG  GLGCGLKNRS  SEGPSSPSGK  LMSPKLYVWA 170         180         190         200
KDRPEIWEGE  PPCLPPRDSL  NQSLSQDLTM  APGSTLWLSC 210         220         230         240
GVPPDSVSRG  PLSWTHVHPK  GPKSLLSLEL  KDDRPARDMW 250         260         270         280
VMETGLLLPR  ATAQDAGKYY  CHRGNLTMSF  HLEITARPVL 290         300         310         320
WHWLLRTGGW  KVSAVTLAYL  IFCLCSLVGI  LHLQRALVLR 330         340         350         360
RKRKRMTDPT  RRFFKVTPPP  GSGPQNQYGN  VLSLPTPTSG 370         380         390         400
LGRAQRWAAG  LGGTAPSYGN  PSSDVQADGA  LGSRSPPGVG 410         420         430         440
PEEEEGEGYE  EPDSEEDSEF  YENDSNLGQD  QLSQDGSGYE 450         460         470         480
DNPEDEPLGPE EDSFSNAES   YENEDEELTQ  PVARTMDFLS 490         500         510         520
PHGSAWDPSR  EATSLGSQSY  EDMRGILYAA  PQLRSIRGQP 530         540         550
GPNHEEDADS  YENMDNPDGP  DPAWGGGGRM  GTWSTR
```

DETAILED DESCRIPTION OF THE INVENTION

Definitions

Figure 1:
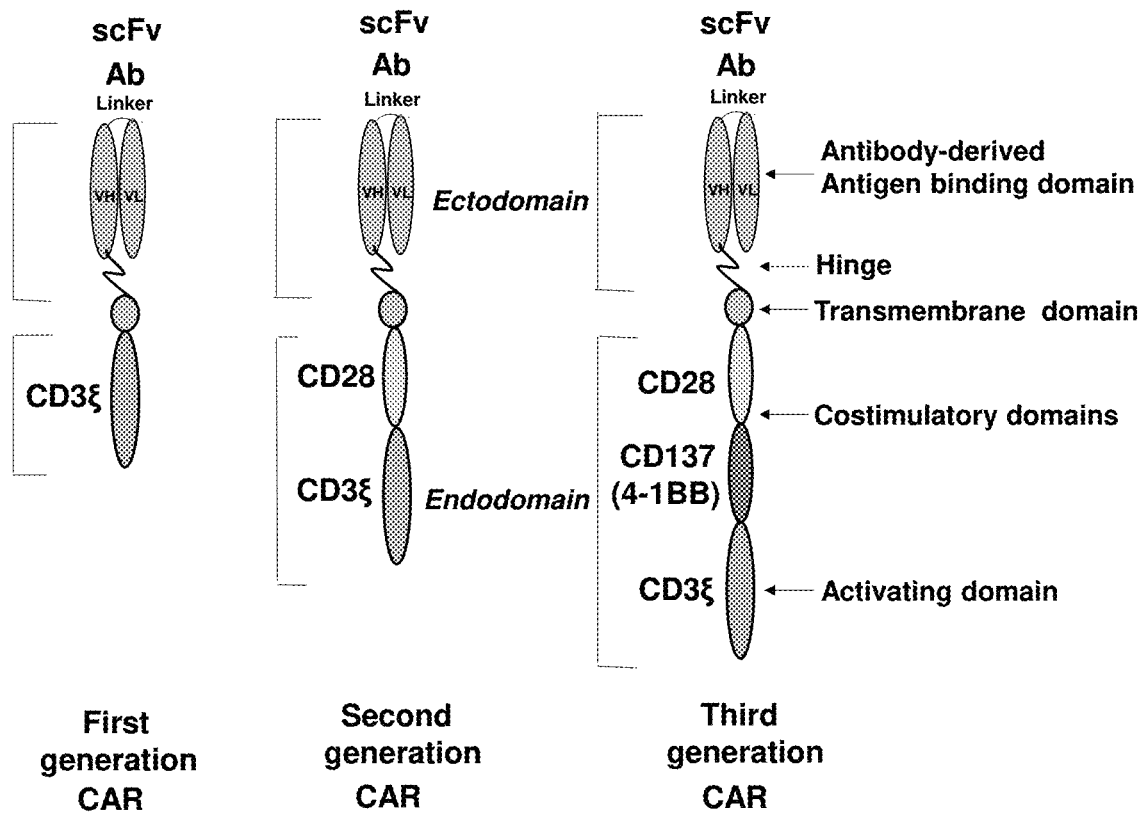
FIG. 1. The structures of CAR

As used herein, a "chimeric antigen receptor (CAR)" is a receptor protein that has been engineered to give T cells the new ability to target a specific protein. The receptor is chimeric because they combine both antigen-binding and T-cell activating functions into a single receptor.

CAR is a fused protein comprising an extracellular domain capable of binding to an antigen, a transmembrane domain, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, "CDRs" are complementary-determining Regions of VH or VL chains of antibody which are critical for binding with antigen.

As used herein, "humanized antibodies" are antibodies from non-human species whose protein sequences have been modified to increase their similarity to antibody variants produced naturally in humans.

As used herein, a "domain" means one region in a polypeptide which is folded into a particular structure independently of other regions.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for engineering an scFv are known to a person skilled in the art.

As used herein, a "tumor antigen" means a biological molecule having antigenicity, expression of which causes cancer.

The inventors have engineered humanized CD19 scFv starting from heavy and light chain variable regions of mouse monoclonal antibody derived from hybridoma cell line FMC63 [6]. The inventors have produced humanized CD19-CAR-T cells to target cancer cells overexpressing CD19 antigen. The humanized CD19-CAR-T cells of the present invention secrete high level of IFN-gamma against leukemia cancer cells. The humanized CD19-CAR-T cells of the present invention kill Hela-CD19-positive target cells but do not kill control Hela cells.

The present invention is directed to a humanized anti-human CD19 antibody, comprising humanized $V_L$ having the amino acid sequence of SEQ ID NO: 5 and humanized $V_H$ having the amino acid sequence of SEQ ID NO: 7, respectively.

In one embodiment, the humanized anti-human CD19 antibody is a single-chain variable fragment (scFv). ScFv can be $V_H$-linker-$V_L$ or $V_L$-linker-$V_H$. Preferred scFv is $V_L$-linker-$V_H$.

The present invention is also directed to a chimeric antigen receptor fusion protein comprising from N-terminus to C-terminus: (i) a single-chain variable fragment (scFv) against CD19 (the present invention), (ii) a transmembrane domain, (iii) at least one co-stimulatory domains, and (iv) an activating domain.

Figure 2:
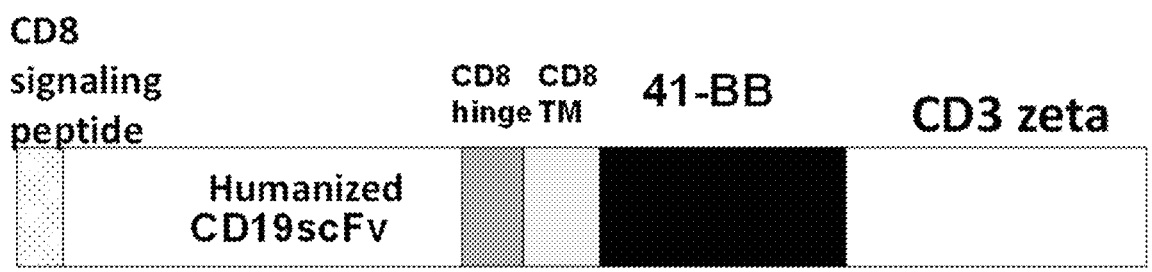
FIG. 2. The structure of humanized CD19-CAR construct. The second generation CD19-CAR is used.

In one embodiment, the CAR structure is shown in FIG. 2.

In one embodiment, the co-stimulatory domain is selected from the group consisting of CD28, 4-1BB, GITR, ICOS-1, CD27, OX-40 and DAP10. A preferred the co-stimulatory domain is CD28.

A preferred activating domain is CD3 zeta (CD3 Z or CD3ζ).

The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain. In one embodiment, a linker sequence having a glycine-serine continuous sequence can be used.

The present invention provides a nucleic acid encoding the CD19-CAR. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBank for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

A nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. A virus vector lacking the replicating ability so as not to self-replicate in an infected cell is preferably used.

For example, when a retrovirus vector is used, a suitable packaging cell based on a LTR sequence and a packaging signal sequence possessed by the vector can be selected for preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

A CAR-T cell binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and it may further comprise a suitable excipient.

The advantages of the humanized CD19-ScFv (clone 6 antibody) of the present invention vs. mouse CD19-ScFv (FMC63) include less immunogenicity to human due to humanized CD19 scFv. Humanized CD19-CAR-T cells of the present invention prolonged survival of mice in Raji xenograft model better than mouse CD19-CAR-T cells.

The present humanized CD19 ScFv can be used for immunotherapy applications: toxin/drug-conjugated antibody, monoclonal therapeutic antibody, and CAR-T cell immunotherapy.

Humanized CD19-CAR-T cells using the present humanized CD19 ScFv effectively target CD19 antigen in CD19-positive cancer cell lines.

Humanized CD19-CAR-T cells can be used in combination with different chemotherapy: checkpoint inhibitors, targeted therapies, small molecule inhibitors, and antibodies.

Humanized CD19-CAR-T cells can be used clinically for CD19-positive cancer cells.

Modifications of co-activation domains such as CD28, 4-1BB and others can be used to increase the efficacy of CAR-T cells. Tag-conjugated humanized CD19 scFv can be used for CAR generation.

Humanized CD19-CAR-T cells can be used with different safety switches such as t-EGFR, RQR (Rituximab-CD34-Rituximab), inducible caspase-9 and other.

Third generation CAR-T or other co-activation signaling domains can be used for the same humanized CD19-scFv to prepare CD19-CAR-T.

The humanized CD19 CAR can be combined with CARs targeting other tumor antigens or tumor microenvironment, e.g., VEGFR-1-3, PDL-1, bi-specific antibodies with CD19 and CD3, or other antigens can be generated for therapy.

The humanized CD19-CAR can be used for generating other types of cells such as CAR-natural killer (NK) cells, CD19-CAR-macrophages, and other CD19-CAR hematopoietic cells, which can target CD19-positive cancers. The present invention provides T cells, or NK cells, or macrophages, or hematopoietic cells, modified to express the CD19-CAR.

The humanized CD19-CAR-T cells can be used against cancer stem cells or tumor initiating cells that are most resistant against chemotherapy and form aggressive tumors.

The following examples further illustrate the present invention. These examples are intended merely to be illustrative of the present invention and are not to be construed as being limiting.

EXAMPLES

The inventors generated humanized CD19-ScFv-CAR constructs inside lentiviral vector cloned into Xba I and Eco R I sites of lentiviral vector. Lentiviral CAR construct containing the humanized CD19 ScFv (clone 6)-41BB-CD3zeta insert—between the Xba I and Eco RI cloning sites.

The lentiviruses were generated in 293T cells and titer was established by RT-PCR. Then equal dose of lentiviruses was used for transduction of T cells.

Example 1. Humanized CD19 $V_H$ and $V_L$ and scFv Sequences

The inventors have humanized CD19 scFv from mouse CD19 FMC63 scFv clone [6], and selected clone 6 based on the efficacy of the in vivo data. The structure of humanized CD19 scFv is: VL-linker-VH.

SEQ ID NO: 2 is the nucleotide sequence of humanized CD19 $V_L$. SEQ ID NO: 4 is the the nucleotide sequence of $V_H$. SEQ ID NO: 3 is nucleotide sequence encoding a linker.

(SEQ ID NO: 2)
gatattcagatgacccagagcccgagcagcctgagcgcgagcgtgggcga tcgcgtgaccattacctgccgcgcgagccaggatattagcaaatatctga actggtatcagcagaaaccgggcaaagcgccgaaactgctgatttatcat accagccgcctgcatagcggcgtgccgagccgctttagcggcagcggcag cggcaccgattttaccctgaccattagcagcctgcagccggaagattttg cgacctattattgccagcagggcaacaccctgccgtatacctttggcggc ggcaccaaagtggaaattaaa (SEQ ID NO: 3)
ggctccacctctggatccggcaagcccggatctggcgagggatccaccaagggc (SEQ ID NO: 4)
gaagtgcagctggtggaaagcggcggcggcctggtgcagccgggcggcag cctgcgcctgagctgcgcggcgagcggcgtgagcctgccggattatggcg tgagctgggtgcgccaggcgccgggcaaaggcctggaatgggtgagcgtg atttggggcagcgaaaccacctattataacagcgcgctgaaaagccgctt taccattagccgcgataacagcaaaaacaccctgtatctgcagatgaaca gcctgcgcgcggaagataccgcggtgtattattgcgcgaaacattattat tatggcggcagctatgcgatggattattggggccagggcaccctggtgac cgtgagcagc SEQ ID NO: 5 is the amino sequence of humanized CD19 $V_L$. SEQ ID NO: 7 is the amino sequence of humanized CD19 $V_H$. SEQ ID NO: 6 is amino acid sequence of a linker. CDR regions are underlined.

(SEQ ID NO: 5)
D I Q M T Q S P S S L S A S V G D R V T I T C
R A S Q D I S K Y L N W Y Q Q K P G K A P K L
L I Y H T S R L H S G V P S R F S G S G S G T
D F T L T I S S L Q P E D F A T Y Y C Q Q G N
T L P Y T F G G G T K V E I K (SEQ ID NO: 6)
G S T S G S G K P G S G E G S T K G (SEQ ID NO: 7)
E V Q L V E S G G G L V Q P G G S L R L S C A
A S G V S L P D Y G V S W V R Q A P G K G L E
W V S V I W G S E T T Y Y N S A L K S R F T I
S R D N S K N T L Y L Q M N S L R A E D T A V
Y Y C A K H Y Y Y G G S Y A M D Y W G Q G T L
V T V S S

SEQ ID NO: 8 shows the amino acid sequence of humanized CD19 scFV of clone 6 ($V_L$-linker-$V_H$)

(SEQ ID NO: 8)
DIQMTQSPSSLSASVGDRVTITCRASQDISKYLNWYQQKPGKAPKLLIYH

TSRLHSGVPSRFSGSGSGTDFTLTISSLQPEDFATYYCQQGNTLPYTFGG

-continued
GTKVEIKGSTSGSGKPGSGEGSTKGEVQLVESGGGLVQPGGSLRLSCAAS

GVSLPDYGVSWVRQAPGKGLEWVSVIWGSETTYYNSALKSRFTISRDNSK

NTLYLQMNSLRAEDTAVYYCAKHYYYGGSYAMDYWGQGTLVTVSS

Example 2. Humanized CD19-CAR Sequences

The scheme of humanized CD19-CAR construct is shown on FIG. 2. Lentiviral vector with EF1a promoter was used for cloning of humanized scFv CAR sequences.

The following nucleotide sequence and amino acid sequence show CD8 leader-humanized CD19 ScFv-CD8 hinge-TM8-41BB-CD3 zeta of the present invention. The CAR structure includes human CD8 signaling peptide, humanized CD19 scFv ($V_L$-Linker-$V_H$), CD8 hinge, CD8 transmembrane (TM), 41BB co-stimulatory and CD3 zeta activation domains (FIG. 2).

<CD8 leader>
Nucleotide
(SEQ ID NO: 9)
ATGGCCTTACCAGTGACCGCCTTGCTCCTGCCGCTGGCCTTGCTGCTCCA

CGCCGCCAGGCCG

Amino-acid
(SEQ ID NO: 10)
MALPVTALLLPLALLLHAARP

<Humanized CD19 scFV, $V_L$-Linker-$V_H$>
See Example 1

<CD8 hinge>
Nucleotide
(SEQ ID NO: 11)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGAT

Amino-acid
(SEQ ID NO: 12)
TTTPAPRPPTPAPTIASQPLSLRPEACRPAAGGAVHTRGLDFACD

<CD8 Transmembrane>
Nucleotide
(SEQ ID NO: 13)
ATCTACATCTGGGCGCCCCTGGCCGGGACTTGTGGGGTCCTTCTCCTGTC

ACTGGTTATCACCCTTTACTGC

Amino-acid
(SEQ ID NO: 14)
IYIWAPLAGTCGVLLLSLVITLYC

<41-BB-co-stimulatory domain>
Nucleotide
(SEQ ID NO: 15)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

Amino-acid
(SEQ ID NO: 16)
KRGRKKLLYIFKQPFMRPVQTTQEEDGCSCRFPEEEEGGCEL

-continued

```
<CD3 zeta>
Nucleotide
                                            (SEQ ID NO: 17)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAATAG

Amino-acid:
                                            (SEQ ID NO: 18)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

<EcoRI restriction site>
gaattc
```

The amino-acid sequence of humanized CD19-4-1BB-CD3-CAR protein is shown below: signaling peptide in italics, linker underlined; CD8 hinge in bold; CD8 TM italics underlined; 41BB in bold italics; CD3 underlined and bold.

```
                                            (SEQ ID NO: 19)
M A L P V T A L L L P L A L L L H A A R P D I Q M

T Q S P S S L S A S V G D R V T I T C R A S Q D I

S K Y L N W Y Q Q K P G K A P K L L I Y H T S R L

H S G V P S R F S G S G S G T D F T L T I S S L Q

P E D F A T Y Y C Q Q G N T L P Y T F G G G T K V

E I K G S T S G S G K P G S G E G S T K G E V Q L

V E S G G G L V Q P G G S L R L S C A A S G V S L

P D Y G V S W V R Q A P G K G L E W V S V I W G S

E T T Y Y N S A L K S R F T I S R D N S K N T L Y

L Q M N S L R A E D T A V Y Y C A K H Y Y Y G G S

Y A M D Y W G Q G T L V T V S S T T T P A P R P P

T P A P T I A S Q P L S L R P E A C R P A A G G A

V H T R G L D F A C D I Y I W A P L A G T C G V L

L L S L V I T L Y C K R G R K K L L

Y I F K Q P F M R P V Q T T Q E E D G C S C R F P

E E E E G G C E L R V K F S R S A D A P A Y K Q G

Q N Q L Y N E L N L G R R E E Y D V L D K R R G R

D P E M G G K P R R K N P Q E G L Y N E L Q K D K

M A E A Y S E I G M K G E R R R G K G H D G L Y Q

G L S T A T K D T Y D A L H M Q A L P P R
```

Example 3. Generation of CAR Lentivirus

DNAs encoding the CARs were synthesized and subcloned into a third-generation lentiviral vector with EF1a promoter. All CAR lentiviral constructs were sequenced in both directions to confirm CAR sequence and used for lentivirus production. Ten million HEK293FT cells (Thermo Fisher) were seeded into T75 flasks and cultured overnight, then transfected with the pPACKH1 Lentivector Packaging mix (System Biosciences, Palo Alto, CA) and 10 μg of each lentiviral vector using the CalPhos Transfection Kit (Takara, Mountain View, CA). The next day the medium was replaced with fresh medium, and 48 h later the lentivirus-containing medium was collected. The medium was cleared of cell debris by centrifugation at 2100 g for 30 min. The virus particles were collected by centrifugation at 112,000 g for 100 min, suspended in AIM V medium, aliquoted and frozen at −80° C. The titers of the virus preparations were determined by quantitative RT-PCR using the Lenti-X qRT-PCR kit (Takara) according to the manufacturer's protocol and the 7900HT thermal cycler (Thermo Fisher). The lentiviral titers were >1×10$^8$ pfu/ml.

Example 4. Generation and Expansion of CAR-T Cells

PBMC were suspended at 1×10$^6$ cells/ml in AIM V-AlbuMAX medium (Thermo Fisher) containing 10% FBS and 300 U/ml IL-2 (Thermo Fisher), mixed with an equal number (1:1 ratio) of CD3/CD28 Dynabeads (Thermo Fisher), and cultured in non-treated 24-well plates (0.5 ml per well). At 24 and 48 hours, lentivirus was added to the cultures at a multiplicity of infection (MOI) of 5, along with 1 μl of TransPlus transduction enhancer (AlStem). As the T cells proliferated over the next two weeks, the cells were counted every 2-3 days and fresh medium with 300 U/ml IL-2 was added to the cultures to maintain the cell density at 1-3×10$^6$ cells/ml.

Example 5. Flow Cytometry

To measure CAR expression, 0.5 million cells were suspended in 100 μl of buffer (PBS containing 0.5% BSA) and incubated on ice with 1 μl of human serum (Jackson Immunoresearch, West Grove, PA) for 10 min. Then 1 μl of allophycocyanin (APC)-labeled anti-CD3 (eBioscience, San Diego, CA), and 2 μl of either phycoerythrin (PE)-labeled Goat anti-mouse or anti-human F(ab)$_2$ or isotype control antibodies were added, and the cells were incubated on ice for 30 min. The cells were rinsed with 3 ml of buffer, then suspended in buffer and acquired on a FACSCalibur (BD Biosciences). Cells were analyzed for CD3 staining versus anti F(Ab)2 staining or isotype control staining.

Example 6. Humanized CD19-CAR-T Cells Expressed CAR

We designed humanized CD19-CAR-T cells with humanized CD19-CAR construct shown in Example 2. We used Mock ScFv with unrelated ScFv and generated Mock-CAR-T cells as a negative control.

After transduction of lentiviral humanized CD19 CAR into T cells, humanized CD19-CAR construct was detected by FACS analysis with goat-anti-human F(ab)$_2$ antibody by FACS as described in [4]. About 60% of CAR-T cells were positive by FACS with anti-human F(ab)$_2$ antibody showing that CAR is expressed and detectable.

Example 7. Humanized CD19-CAR-T Cells Killed Hela-CD19 Cells but not Hela Cells We incubated humanized effector CD19-CAR-T cells of the present invention with target Hela-CD19 target cells and also Hela (CD19-negative) control cells and performed real-time cytotoxicity assay (RTCA), as described in [4].

Figure 3:
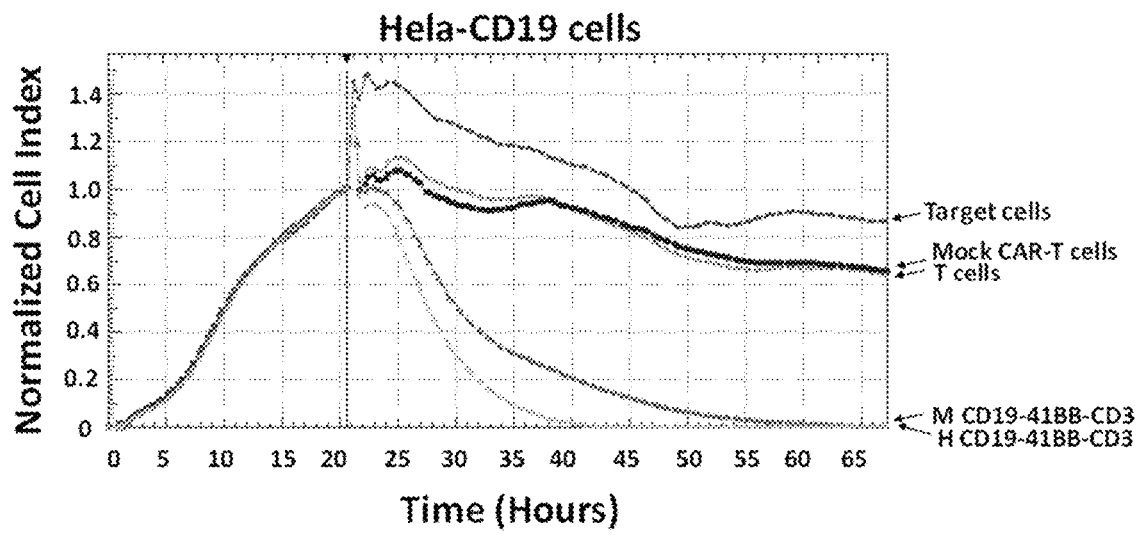
FIG. 3. Humanized CD19-CAR-T cells killed Hela-CD19 cells. XCelligence Real-time cytotoxicity assay was used for detection of humanized CD19-CAR-T and mouse CD19-41BB-CD3 CAR-T cell cytotoxicity, as described [4]. Normalized cell index is shown on Y-axis, and time in hours is shown on X-axis. From top to bottom on the right, Target cells alone; then effector cells added to target cells: T cells, Mock CAR-T cells, Mouse (M) CD19-CAR-T cells, Humanized (H) CD19 CAR-T cells.

Humanized CD19-CAR-T cells specifically killed Hela-CD19 cells as the number of target cell (cell index) significantly decreased by CAR-T cells, but not by T cells or Mock CAR-T cells (FIG. 3).

In a separate experiment, humanized CD19-CAR-T cells did not kill CD19-negative Hela cells, and there was no significant difference between T cells, Mock CAR-T cells and CAR-T cells in killing CD19-negative Hela cells. This demonstrates high specificity of humanized CD19-CAR-T cells to target CD19 antigen and to kill only CD19-positive cells but not CD19-negative Hela cells (Data not shown).

Figure 4:
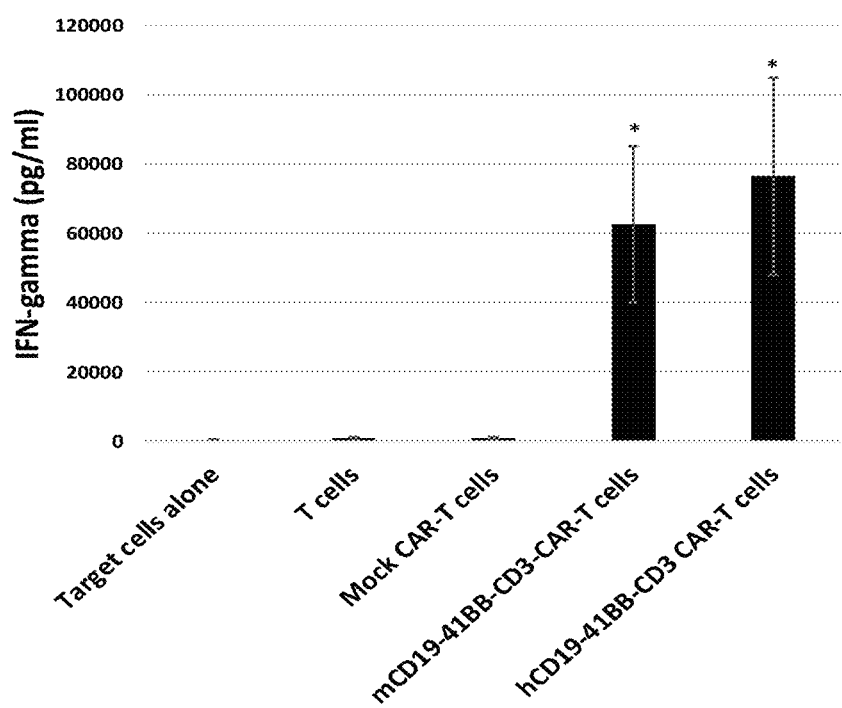
FIG. 4. Humanized CD19-CAR-T cells secreted IFN-gamma with Hela-CD19-positive cells. *: p<0.05, IFN-gamma secreted by humanized CAR-T cells and mouse CD19-CAR-T cells, versus T cells, Mock CAR-T cells in Hela-CD19 cells.

Example 8. Humanized CAR-T Cells Secreted IFN-Gamma Against Target Hela-CD19 Cells We collected supernatant after co-incubation of humanized CD19-CAR-T cells with target Hela-CD19 and performed IFN-gamma assay, as described [5]. Humanized CD19-CAR-T cells secreted IFN-gamma with Hela-CD19 significantly higher than that secreted by T cells and Mock CAR-T cells (FIG. 4). The level of IFN-gamma secreted by humanized CD19-CAR-T cells was comparable with mouse CD19-CAR-T cells suggesting their similar activity in secreting IFN-gamma (FIG. 4).

Figure 5:
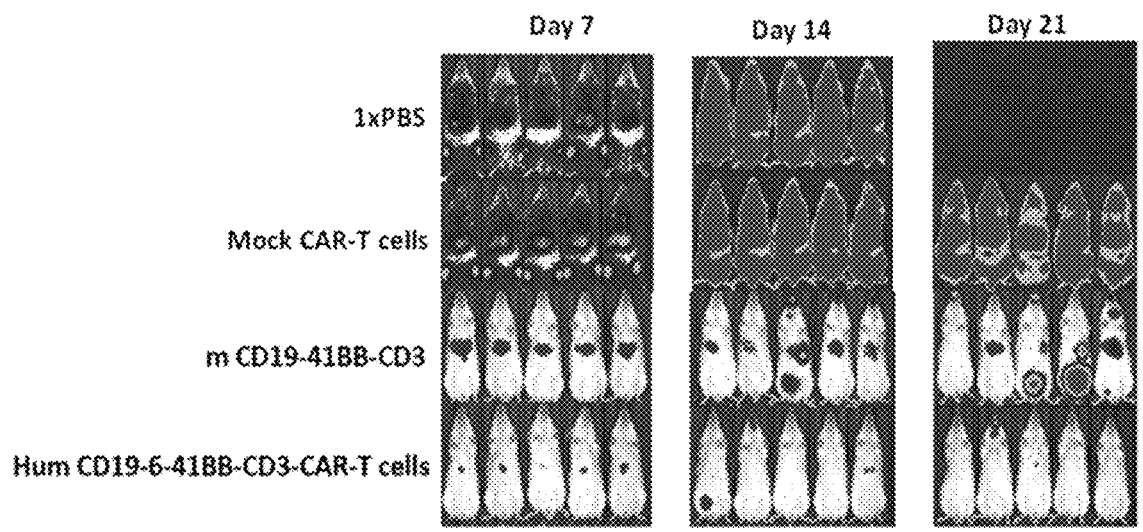
FIG. 5. Humanized CD19-CAR-T cells and mouse CD19-CAR-T cells significantly decreased mouse xenograft tumor growth by imaging.

Example 9. Humanized CD19-CAR-T Cells Decreased Raji Xenograft Tumor Growth In Vivo We injected Raji-luciferase-positive cells into NSG-mice intravenously and then next day injected 1×10$^7$ humanized CD19-CAR-T cells, as described in [4]. We used IVIS system to detect Raji xenograft tumor cell growth by imaging. Humanized CD19-CAR-T cells significantly decreased Raji xenograft growth compared to control PBS and Mock-CAR-T cells (FIG. 5). The decreased Raji tumor growth was more pronounced with humanized CD19-CAR-T cells than with mouse CD19-CAR-T cells (FIG. 5).

Figure 6:
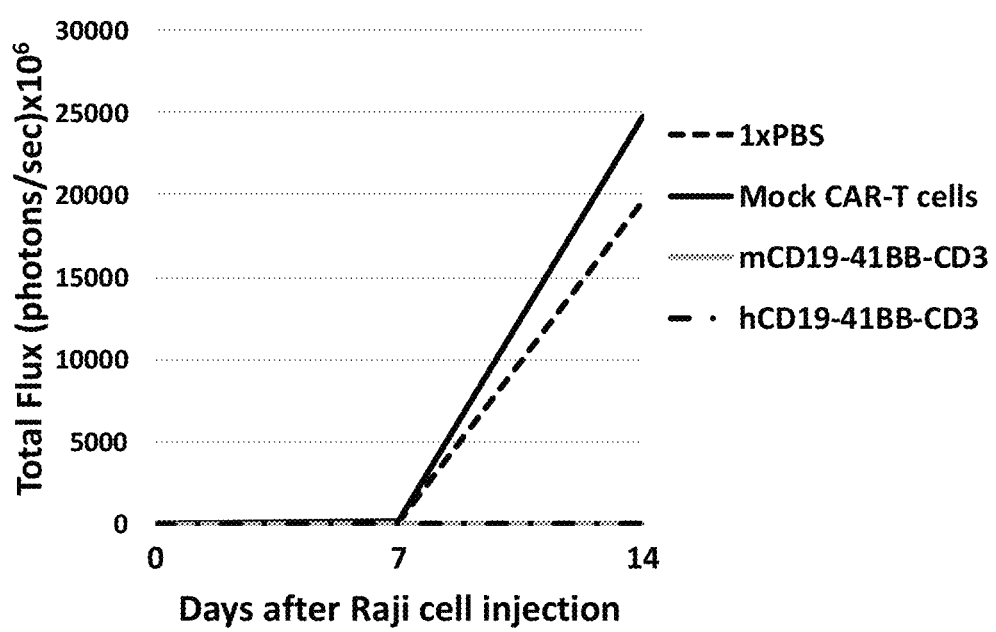
FIG. 6. Humanized CD19-CAR-T cells significantly decreased total flux (imaging signal) of Raji-luciferase xenograft tumors in NSG mice model in vivo. Humanized CAR-T cells and mouse CD19-CAR-T cells showed total flux at about baseline. *p<0.0001, CD19-CAR-T cells vs. Mock, PBS treated mice.

The quantification of imaging at day 14 is shown in FIG. 6, which shows that both mouse and humanized CD19-CAR-T cells significantly decrease the imaging signal-total flux in photons/sec.

Figure 7:
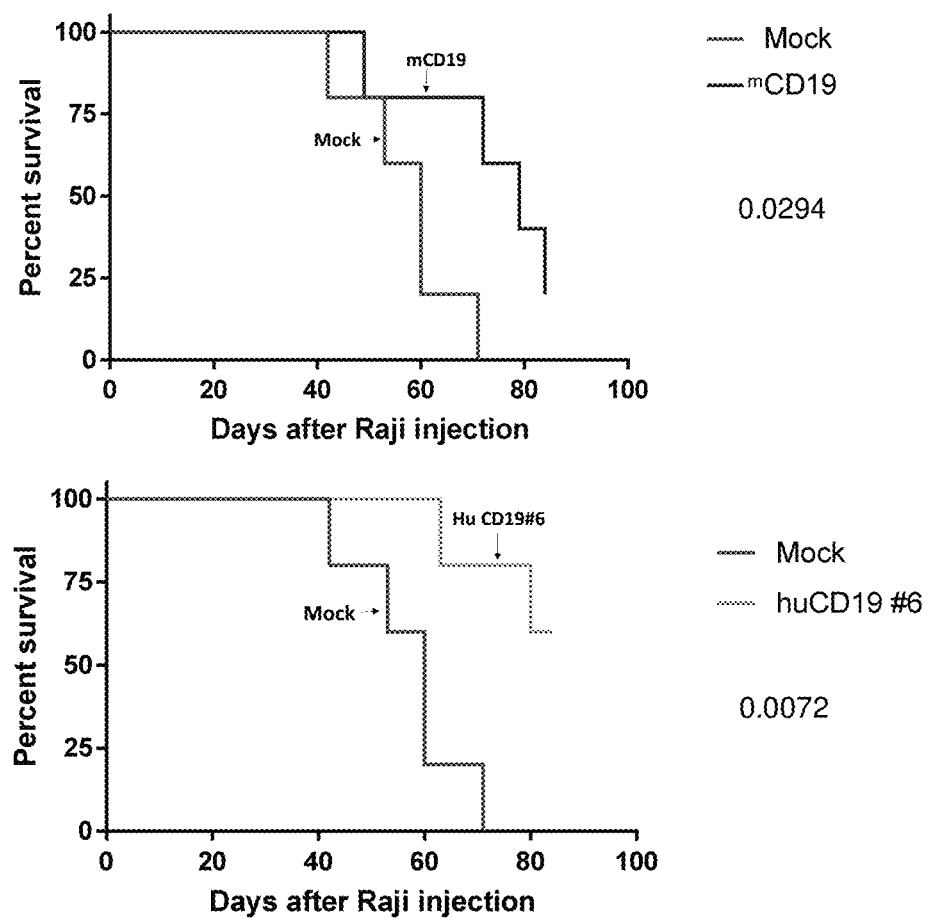
FIG. 7. Humanized CD19-CAR-T cells significantly prolonged survival of mice in Raji xenograft model. Kaplan-Meier survival curve shows that humanized (h) CD19-CAR-T cells and mouse (m) CD19-CAR-T cells significantly prolonged survival of mice versus Mock CAR-T cells. CAR-T cells were injected by i.v 1×10^7 cells/mice. *p=0.0072, hCD19-41Bb-CD3 CAR-T cells vs Mock CAR-T cells (bottom panel); p=0.0294, mCD19-41BB-CD3 CAR-T cells vs Mock-CAR-T cells (upper panel).

Example 10. Humanized CD19-CAR-T Cells Prolonged Survival of Mice in Raji Xenograft Model Over Mice Treated with Mouse CD19-CAR-T Cells The Kaplan-Myer survival curve of the results of Example 9 shows a significant increase of mouse survival after injecting humanized CD19-CAR-T cells (clone 6) compared with control Mock-treated mouse. The survival was increased more significantly by humanized CD19-CAR-T cells (p=0.0072) (FIG. 7, lower panel) than by mouse CD19-CAR-T cells (p=0.0294) versus Mock CAR-T cells (FIG. 7, top panel) This demonstrates advantage of increased efficacy of humanized CD19-CAR-T cells compared with mouse CD19-CAR-T cells.

Example 11. CD19-CAR-T Cells are Detected by FACS with CD19 or FAB Antibody after Injection into Mice In Vivo Seven days after injecting humanized CD19-CAR-T cells or mouse CD19-CAR-T cells into mice having Raji xenograft tumor cells, mice blood was collected to test the presence of CD19-CAR-T cells. Rabbit anti-FMC63 antibody was used to detect mouse CD19-CAR-T cells. Goat anti-human (Fab'2) antibody (Promab Biotechnologies, Inc.) was used to detect humanized CD19-CAR-T cells.

Figure 8:
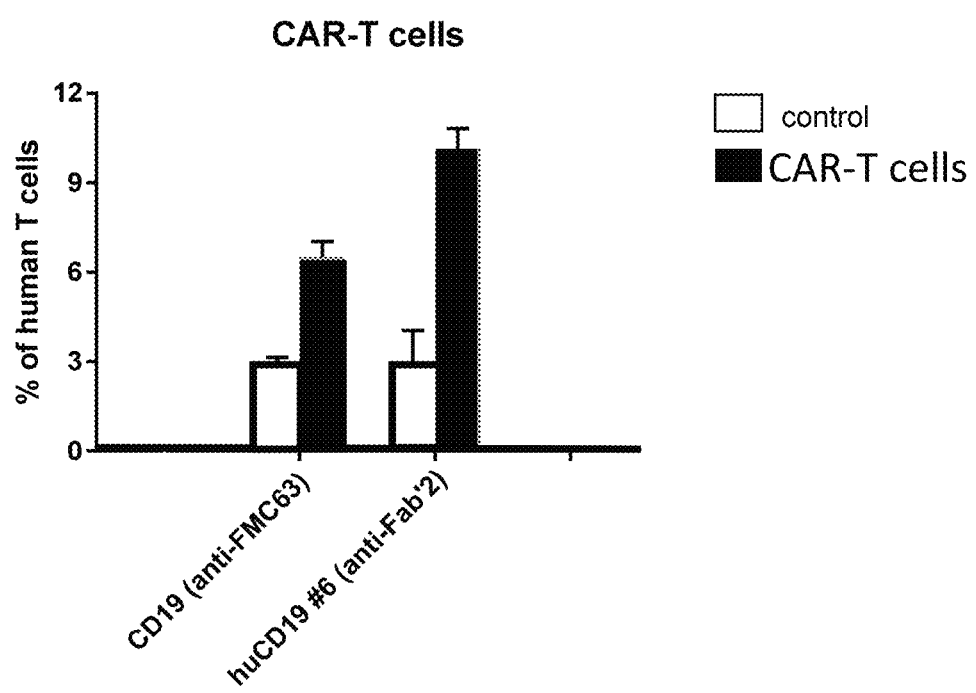
FIG. 8. Humanized CD19-CAR-T cells (clone 6 antibody) and mouse CD19-CAR-T cells (FMC63 antibody) were detected in mouse blood after injecting CAR-T cells into mice. Rabbit anti-FMC63 antibody detected mouse CD19-CAR-T cells; goat anti-human (Fab)$_2$ antibody detected humanized CD19-CAR-T cells. Control is Mock CAR-T cells.

The results are shown in FIG. 8. Both humanized CD19-CAR-T cells and mouse CD19-CAR-T cells were readily detected after 7 days injecting into mice. The persistence of humanized CD19-CAR-T was better than that of mouse-CAR-T cells. The persistence of CAR-T cells in vivo is consistent with significantly decreased Raji xenograft tumor growth.

REFERENCES

1. Maus, M. V.; Haas, A. R.; Beatty, G. L.; Albelda, S. M.; Levine, B. L.; Liu, X.; Zhao, Y.; Kalos, M.; June, C. H. T cells expressing chimeric antigen receptors can cause anaphylaxis in humans. *Cancer Immunol Res* 2013, 1, 26-31.
2. Maus, M. V.; Grupp, S. A.; Porter, D. L.; June, C. H. Antibody-modified t cells: Cars take the front seat for hematologic malignancies. *Blood* 2014, 123, 2625-2635.
3. Eshhar, Z.; Waks, T.; Gross, G. The emergence of t-bodies/car t cells. *Cancer J* 2014, 20, 123-126.
4. Berahovich, R.; Xu, S.; Zhou, H.; Harto, H.; Xu, Q.; Garcia, A.; Liu, F.; Golubovskaya, V. M.; Wu, L. Flag-tagged cd19-specific car-t cells eliminate cd19-bearing solid tumor cells in vitro and in vivo. *Front Biosci (Landmark Ed)* 2017, 22, 1644-1654.
5. Golubovskaya, V.; Berahovich, R.; Zhou, H.; Xu, S.; Harto, H.; Li, L.; Chao, C. C.; Mao, M. M.; Wu, L. Cd47-car-t cells effectively kill target cancer cells and block pancreatic tumor growth. *Cancers (Basel)* 2017, 9.
6. Nicholson, et al., Molecular Immunology, 1997, 34: 1157-1165.

What is claimed is:

1. A humanized anti-human CD19 antibody comprising $V_L$ having the amino acid of SEQ ID NO: 5 and $V_H$ having the amino acid of SEQ ID NO: 7.

2. A single-chain variable fragment (scFv) comprising $V_L$ having the amino acid of SEQ ID NO: 5 and $V_H$ having the amino acid of SEQ ID NO: 7.

3. The scFv of claim 2, further comprises a linker in between VH and VL.

4. The scFv of claim 2, which comprises the amino acid sequence of SEQ ID NO: 8.

5. A chimeric antigen receptor (CAR) comprising from N-terminus to C-terminus:
    (i) the scFv of claim 2,
    (ii) a transmembrane domain,
    (iii) at least one co-stimulatory domains, and
    (iv) an activating domain.

6. The CAR according to claim 5, wherein the co-stimulatory domain is CD28 or 4-1BB.

7. The CAR according to claim 5, wherein the activation domain is CD3 zeta.

8. The CAR of claim 5, which has the amino acid sequence of SEQ ID NO: 19.

9. A nucleic acid encoding the CAR of claim 5.

10. A nucleic acid encoding the CAR of claim 8.

11. T cells modified to express the CAR of claim 5.

12. T cells modified to express the CAR of claim 8.

13. Natural killer cells modified to express the CAR of claim 5.

14. Natural killer cells modified to express the CAR of claim 8.

* * * * *

SEQUENCE LISTING

<160> NUMBER OF SEQ ID NOS: 19

<210> SEQ ID NO 1
<211> LENGTH: 556
<212> TYPE: PRT
<213> ORGANISM: Homo sapiens

<400> SEQUENCE: 1

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400
```

```
Pro Glu Glu Glu Gly Gly Tyr Glu Pro Asp Ser Glu Glu
            405                 410             415
Asp Ser Glu Phe Tyr Glu Asn Asp Ser Asn Leu Gly Gln Asp Gln Leu
            420                 425                 430
Ser Gln Asp Gly Ser Gly Tyr Glu Asn Pro Glu Asp Glu Pro Leu Gly
            435                 440                 445
Pro Glu Asp Glu Asp Ser Phe Ser Asn Ala Glu Ser Tyr Glu Asn Glu
            450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Gly
                485                 490                 495
Ser Gln Ser Tyr Glu Asp Met Arg Gly Ile Leu Tyr Ala Ala Pro Gln
                500                 505                 510
Leu Arg Ser Ile Arg Gly Gln Pro Gly Pro Asn His Glu Glu Asp Ala
                515                 520                 525
Asp Ser Tyr Glu Asn Met Asp Asn Pro Asp Gly Pro Asp Pro Ala Trp
            530                 535                 540
Gly Gly Gly Gly Arg Met Gly Thr Trp Ser Thr Arg
545                 550                 555

<210> SEQ ID NO 2
<211> LENGTH: 321
<212> TYPE: DNA
<213> ORGANISM: Homo sapiens

<400> SEQUENCE: 2
gatattcaga tgacccagag cccgagcagc ctgagcgcga gcgtgggcga tcgcgtgacc     60
attacctgcc gcgcgagcca ggatattagc aaatatctga actggtatca gcagaaaccg    120
ggcaaagcgc cgaaactgct gatttatcat accagccgcc tgcatagcgg cgtgccgagc    180
cgctttagcg gcagcggcag cggcaccgat tttaccctga ccattagcag cctgcagccg    240
gaagattttg cgacctatta ttgccagcag ggcaacaccc tgccgtatac ctttggcggc    300
ggcaccaaag tggaaattaa a                                              321

<210> SEQ ID NO 3
<211> LENGTH: 54
<212> TYPE: DNA
<213> ORGANISM: Artificial Sequence
<220> FEATURE:
<223> OTHER INFORMATION: synthetic

<400> SEQUENCE: 3
ggctccacct ctggatccgg caagcccgga tctggcgagg atccaccaa gggc            54

<210> SEQ ID NO 4
<211> LENGTH: 360
<212> TYPE: DNA
<213> ORGANISM: Homo sapiens

<400> SEQUENCE: 4
gaagtgcagc tggtggaaag cggcggcggc ctggtgcagc cgggcggcag cctgcgcctg     60
agctgcgcgg cgagcggcgt gagcctgccg gattatggcg tgagctgggt gcgccaggcg    120
ccgggcaaag gcctggaatg ggtgagcgtg atttggggca gcgaaaccac ctattataac    180
agcgcgctga aaagccgctt taccattagc cgcgataaca gcaaaaacac cctgtatctg    240
```

-continued

```
cagatgaaca gcctgcgcgc ggaagatacc gcggtgtatt attgcgcgaa acattattat    300
tatggcggca gctatgcgat ggattattgg ggccagggca ccctggtgac cgtgagcagc    360
```

```
<210> SEQ ID NO 5
<211> LENGTH: 107
<212> TYPE: PRT
<213> ORGANISM: Homo sapiens

<400> SEQUENCE: 5
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys
            100                 105

```
<210> SEQ ID NO 6
<211> LENGTH: 18
<212> TYPE: PRT
<213> ORGANISM: Artificial Sequence
<220> FEATURE:
<223> OTHER INFORMATION: synthetic

<400> SEQUENCE: 6
```

Gly Ser Thr Ser Gly Ser Gly Lys Pro Gly Ser Gly Glu Gly Ser Thr
1               5                   10                  15

Lys Gly

```
<210> SEQ ID NO 7
<211> LENGTH: 120
<212> TYPE: PRT
<213> ORGANISM: Homo sapiens

<400> SEQUENCE: 7
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ser Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 8
<211> LENGTH: 245
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Val Ser Leu Pro Asp Tyr Gly Val Ser
145                 150                 155                 160

Trp Val Arg Gln Ala Pro Gly Lys Gly Leu Glu Trp Val Ser Val Ile
                165                 170                 175

Trp Gly Ser Glu Thr Thr Tyr Tyr Asn Ser Ala Leu Lys Ser Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Lys His Tyr
210                 215                 220

Tyr Tyr Gly Gly Ser Tyr Ala Met Asp Tyr Trp Gly Gln Gly Thr Leu
225                 230                 235                 240

Val Thr Val Ser Ser
            245

<210> SEQ ID NO 9
<211> LENGTH: 63
<212> TYPE: DNA
<213> ORGANISM: Homo sapiens

<400> SEQUENCE: 9
atggccttac cagtgaccgc cttgctcctg ccgctggcct tgctgctcca cgccgccagg      60
ccg                                                                   63

<210> SEQ ID NO 10
<211> LENGTH: 21
<212> TYPE: PRT
<213> ORGANISM: Homo sapiens

<400> SEQUENCE: 10

Met Ala Leu Pro Val Thr Ala Leu Leu Leu Pro Leu Ala Leu Leu Leu
1               5                   10                  15

His Ala Ala Arg Pro
            20

<210> SEQ ID NO 11
<211> LENGTH: 135
<212> TYPE: DNA
<213> ORGANISM: Homo sapiens

<400> SEQUENCE: 11
accacgacgc cagcgccgcg accaccaaca ccggcgccca ccatcgcgtc gcagcccctg      60
tccctgcgcc cagaggcgtg ccggccagcg gcggggggcg cagtgcacac gaggggggctg    120 gacttcgcct gtgat                                                     135

<210> SEQ ID NO 12
<211> LENGTH: 45
<212> TYPE: PRT
<213> ORGANISM: Homo sapiens

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 13
<211> LENGTH: 72
<212> TYPE: DNA
<213> ORGANISM: Homo sapiens

<400> SEQUENCE: 13
atctacatct gggcgcccct ggccgggact tgtggggtcc ttctcctgtc actggttatc      60
accctttact gc                                                         72

<210> SEQ ID NO 14
<211> LENGTH: 24
<212> TYPE: PRT
<213> ORGANISM: Homo sapiens

<400> SEQUENCE: 14

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 15
<211> LENGTH: 126
<212> TYPE: DNA
<213> ORGANISM: Homo sapiens

<400> SEQUENCE: 15
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 16
<211> LENGTH: 42
<212> TYPE: PRT

```
<213> ORGANISM: Homo sapiens

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 342
<212> TYPE: DNA
<213> ORGANISM: Homo sapiens

<400> SEQUENCE: 17
agagtgaagt tcagcaggag cgcagacgcc ccgcgtaca agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc     240
cggaggggca aggggcacga tggcctttac cagggtctca gtacagccac caaggacacc    300
tacgacgccc ttcacatgca ggccctgccc cctcgctaat ag                      342

<210> SEQ ID NO 18
<211> LENGTH: 112
<212> TYPE: PRT
<213> ORGANISM: Homo sapiens

<400> SEQUENCE: 18

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 489
<212> TYPE: PRT
<213> ORGANISM: Homo sapiens

<400> SEQUENCE: 19

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45
```

```
Asp Ile Ser Lys Tyr Leu Asn Trp Tyr Gln Gln Lys Pro Gly Lys Ala
 50                  55                  60

Pro Lys Leu Leu Ile Tyr His Thr Ser Arg Leu His Ser Gly Val Pro
 65                  70                  75                  80

Ser Arg Phe Ser Gly Ser Gly Ser Gly Thr Asp Phe Thr Leu Thr Ile
                 85                  90                  95

Ser Ser Leu Gln Pro Glu Asp Phe Ala Thr Tyr Tyr Cys Gln Gln Gly
                100                 105                 110

Asn Thr Leu Pro Tyr Thr Phe Gly Gly Gly Thr Lys Val Glu Ile Lys
                115                 120                 125

Gly Ser Thr Ser Gly Ser Gly Lys Pro Gly Ser Gly Glu Gly Ser Thr
130                 135                 140

Lys Gly Glu Val Gln Leu Val Glu Ser Gly Gly Gly Leu Val Gln Pro
145                 150                 155                 160

Gly Gly Ser Leu Arg Leu Ser Cys Ala Ala Ser Gly Val Ser Leu Pro
                165                 170                 175

Asp Tyr Gly Val Ser Trp Val Arg Gln Ala Pro Gly Lys Gly Leu Glu
                180                 185                 190

Trp Val Ser Val Ile Trp Gly Ser Glu Thr Thr Tyr Tyr Asn Ser Ala
                195                 200                 205

Leu Lys Ser Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Lys His Tyr Tyr Gly Gly Ser Tyr Ala Met Asp Tyr Trp
                245                 250                 255

Gly Gln Gly Thr Leu Val Thr Val Ser Ser Thr Thr Thr Pro Ala Pro
                260                 265                 270

Arg Pro Pro Thr Pro Ala Pro Thr Ile Ala Ser Gln Pro Leu Ser Leu
                275                 280                 285

Arg Pro Glu Ala Cys Arg Pro Ala Ala Gly Gly Ala Val His Thr Arg
                290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
                355                 360                 365

Glu Glu Glu Glu Gly Gly Cys Glu Leu Arg Val Lys Phe Ser Arg Ser
                370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Gly Lys Gly His Asp
450                 455                 460
```

```
Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```